United States Patent
Kumar et al.

(10) Patent No.: US 9,846,147 B2
(45) Date of Patent: Dec. 19, 2017

(54) PREDICTION OF REFINING CHARACTERISTICS OF OIL

(71) Applicant: BHARAT PETROLEUM CORPORATION LTD., Mumbai (IN)

(72) Inventors: Rajeev Kumar, Greater Noida (IN); Mohammad Muzaffar Ahsan, Greater Noida (IN); Prashant Udaysinh Parihar, Greater Noida (IN); Ravi Kumar Voolapalli, Greater Noida (IN)

(73) Assignee: Bharat Petroleum Corporation Ltd., Mumbai (IN)

( * ) Notice: Subject to any disclaimer, the term of this patent is extended or adjusted under 35 U.S.C. 154(b) by 907 days.

(21) Appl. No.: 14/005,425

(22) PCT Filed: Oct. 31, 2012

(86) PCT No.: PCT/IN2012/000717
§ 371 (c)(1),
(2) Date: Sep. 16, 2013

(87) PCT Pub. No.: WO2013/102916
PCT Pub. Date: Jul. 11, 2013

(65) Prior Publication Data
US 2014/0156241 A1 Jun. 5, 2014

(30) Foreign Application Priority Data
Jan. 6, 2012 (IN) .............................. 58/MUM/2012

(51) Int. Cl.
*G06G 7/48* (2006.01)
*G06G 7/58* (2006.01)
*G01N 33/28* (2006.01)

(52) U.S. Cl.
CPC ......... *G01N 33/28* (2013.01); *G01N 33/2823* (2013.01); *G01N 33/2835* (2013.01)

(58) Field of Classification Search
CPC . G01N 33/28; G01N 33/2823; G01N 33/2835
(Continued)

(56) References Cited

U.S. PATENT DOCUMENTS

| | | | |
|---|---|---|---|
| 5,841,678 A * | 11/1998 | Hasenberg | C10G 45/72 700/29 |
| 2010/0122934 A1* | 5/2010 | Haizmann | C10G 21/003 208/86 |
| 2010/0243518 A1* | 9/2010 | Zimmerman | C10G 67/049 208/45 |

OTHER PUBLICATIONS

Hassan et al. (Improving oil refinery productivity through enhancement crude blending using linear programming modeling, 2011 (20 pages)).*

(Continued)

*Primary Examiner* — Andre Pierre Louis
(74) *Attorney, Agent, or Firm* — Barnes & Thornburg LLP

(57) ABSTRACT

Method(s) and a system for predicting the refining characteristics of an oil sample are described. The method of predicting the refining characteristics, such as distillate yield profile, processability, product quality or refinery processing cost, may include development of a prediction model based on regression analysis. The method may further include determining the physical properties of the oil sample and predicting the refining characteristics based on the developed prediction model. The determination of the physical properties of the oil sample includes determining at least one of Conradson Carbon Residue (CCR) content, Ramsbottom Carbon Residue (RCR) and Micro Carbon Residue (MCR).

20 Claims, 10 Drawing Sheets

(58) Field of Classification Search
USPC .................................................... 703/6, 12
See application file for complete search history.

(56) References Cited

OTHER PUBLICATIONS

Canavesi et al. (EP 2071329 A2) teaches a method for predicting a parameter of a bitumen and relative prevision system.*

* cited by examiner

PREDICTION OF REFINING CHARACTERISTICS OF OIL

CROSS-REFERENCE TO RELATED APPLICATIONS

This application is a national stage entry under 35 U.S.C. §371(b) of International Application No. PCT/IN2012/000717, filed Oct. 31, 2012, which claims the benefit of Indian Patent Application Serial No. 58/MUM/2012, filed Jan. 6, 2012, the disclosures of which are hereby incorporated herein by reference.

FIELD OF INVENTION

The present invention relates to a method of prediction of refining characteristics of oil and, in particular, relates to prediction of refining characteristics based on physical properties of the oil.

BACKGROUND

Crude oil generally refers to a complex mixture of hydrocarbons which is obtained from geological formations beneath the earth, and from which refined petroleum products can be obtained through fractional distillation. Fractional distillation in a refinery is a multi-step process. Each step in the process yields different products in the form of distillates and residues at different boiling ranges. Crude oils vary considerably from each other in yields of these products and in properties of the yields obtained. A detailed analysis of crude oil characteristics, such as probable yields, blends, pricing, processability, hydrogen consumption in hydro processing, quality, residue-potential, and the like, is used for the purpose of making business decisions, and for planning, controlling and optimization of refinery operations. Such characteristics of a crude oil will be herein referred to as refining characteristics.

The refining characteristics help not only in taking business decisions for a crude oil sample, but are also a source for meeting refinery constraints, product demand and specifications, predicting distillates and residue yields, predicting processing costs, routing of intermediate distillate streams for maximum profits, and hydrogen management.

The conventional methods for evaluating the refining characteristics of crude oils either involve laboratory distillation of an oil sample or detailed molecular and spectroscopic analysis based on, for example, Nuclear magnetic resonance (NMR) spectroscopy, Gas Chromatography-Mass Spectroscopy (GC-MS), Infrared (IR) spectroscopy and Ultraviolet (UV) spectroscopy. The spectroscopic methods exploit the magnetic properties and the spectra of light for certain atomic nuclei to determine the chemical and physical properties of the sample in which they are contained.

SUMMARY

This summary is provided to introduce concepts related to prediction of refining characteristics of a given oil sample, which is further described below in the detailed description. This summary is not intended to identify essential features of the claimed subject matter nor is it intended for use in determining or limiting the scope of the claimed subject matter.

In one embodiment of the present subject matter, method(s) and system(s) for predicting refining characteristics of an oil sample are described. The method of predicting the refining characteristics may include development of a prediction model based on regression. The method may further include determining physical properties of the oil sample and predicting the refining characteristics based on the developed prediction model. The determination of the physical properties of the oil sample includes determining at least one of Conradson Carbon Residue (CCR) content, Ramsbottom Carbon Residue (RCR) and Micro Carbon Residue (MCR).

BRIEF DESCRIPTION OF DRAWINGS

The detailed description is provided with reference to the accompanying figures. In the figures, the left-most digit(s) of a reference number identifies the figure in which the reference number first appears. The same numbers are used throughout the drawings to reference like features and components.

FIG. 9 (b) illustrates a graph showing ranking of crude oils vis-à-vis Brent crude oil pricing, in accordance with an implementation of the present subject matter.

DETAILED DESCRIPTION

Figure 1:
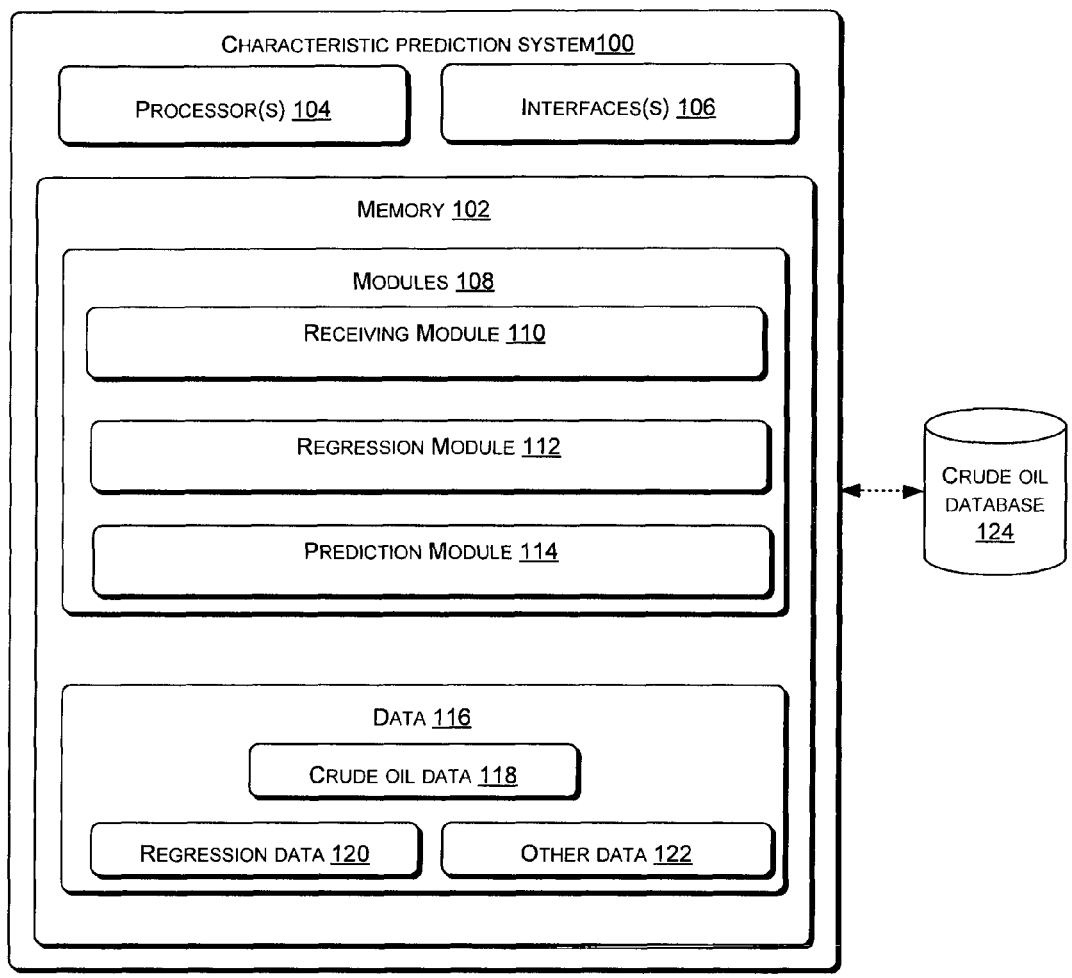
FIG. 1 illustrates a refining characteristics prediction system, in accordance with an implementation of the present subject matter.

The present subject matter, relates to a method of predicting the refining characteristics of an oil sample. The oil sample may include, for example, a crude oil, crude oil blends, synthetic oils and hydrocarbon mixtures. While the following description uses crude oil as an example, it will be understood that any of the aforementioned types of oil sample may also be used, as would be evident to a person skilled in the art. There are various varieties of crude oils that are available in the petroleum market, of which Bombay High crude, Arab Light, and Saharan Blend Crude oil are prominent examples. Every oil variety differs from the other in terms of composition and properties. Thus, the amount and quality of distillates and residues also differ. Generally, a detailed estimate of refining characteristics of the oil may be used for the planning and optimization of refinery operations and profitability.

Conventional methods available for determining refining characteristics of an oil sample may include methods like laboratory distillation or spectroscopic examination, such as by Nuclear Magnetic Resonance (NMR) spectroscopy, Infrared (IR) spectroscopy, Gas Chromatography-Mass Spectroscopy (GC-MS), and the like.

Laboratory experimental data of true boiling point (TBP) distillation is currently the closest representation of refinery distillation profile. TBP distillation in a laboratory is basically a batch distillation operation following ASTM D2892 and D5236 methods in combination. This is used for fractionation of crude oils and for generating samples for cut-wise analyses for detailed characterization of oil. Hence, the data obtained from such TBP distillation and cut-wise analyses is also called crude assay data. The detailed crude assay data contains accurate estimates of distillation profile and product qualities. While this is an accurate method for representing the refinery distillate, residue profile and product qualities, data, it is a costly and time consuming process. It typically costs over USD 30,000 per batch and takes four to six weeks to complete for each batch.

The spectroscopic methods, on the other hand, may give detailed information regarding the molecular composition and overall properties of the oil sample faster, but the accuracy may vary over a large range based on factors, such as sensitivity of the oil sample for different properties, molecular functional groups present in the oil, and the like. Further, the accuracy of the spectroscopic methods may also depend upon the differences in geological, physical and chemical properties of the unknown or target oil sample and the reference crude oil used for prediction of these properties. If the target oil sample is similar to the reference crude oil assay, in terms of geological, chemical or physical properties, then the predicted properties would also be similar to the actual properties of the oil sample. However, if the target oil sample is very different from the reference crude oil assay, the predicted properties may have large deviations from the actual properties. Further, the spectroscopic methods do not provide the details of the refining characteristics, such as yield profile, of the oil sample, but only provide estimates of the properties of the oil sample.

As mentioned above, a detailed analysis of crude oil refining characteristics, such as probable yields, blends, processability, hydrogen consumption in hydro processing, quality, residue-potential, and the like, is used for the purposes of making financial and operational business decisions. For example, estimation of the distillate and residue yield profile can be used for planning and optimization of refinery operations and profitability, and for determining other refining characteristics.

In accordance with the present subject matter, a method for predicting the refining characteristics for any given oil sample is described. The method is used to predict the refining characteristics for the oil sample by measurement of physical properties of the oil sample. The method uses a prediction model in order to predict the refining characteristics for the oil sample, including residue and distillate profile, accurately and quickly. In one implementation, the coefficients in the prediction model are determined based on correlation regression, and hence the prediction model may also be referred to as correlation model.

The method described herein, is based on the measurement of one or more physical properties, including at least one of Conradson Carbon Residue (CCR) content, Ramsbottom Carbon Residue (RCR) and Micro Carbon Residue (MCR), of the oil sample and then predicting the refining characteristics with the help of a prediction model. It has been found that the use of carbon content of the oil, as measured by at least one of CCR, RCR and MCR, along with other physical properties, such as API gravity and Suplhur content, helps in better prediction of the refining characteristics than when the other physical parameters are used without considering the carbon content.

The prediction model for a refining characteristic is generated based on coefficients obtained by regression between measured physical properties and measurement of the refining characteristic for known crude oils. Measured properties of the unknown oil sample act as an input for the prediction model. These inputs, when substituted in the regression equations with the previously obtained coefficients of the prediction model, give an output which includes one or more refining characteristics, such as yield profile, product quality and specifications, hydrogen consumption in hydro processing, routing of intermediate refinery distillate streams, secondary unit processing, capacity utilization, pricing and the like for the oil sample.

In one implementation, the output can be plotted against the measured physical properties on the basis of known temperature ranges of the distillate and residues for the oil sample. Thus, detailed information regarding the refining characteristics of the oil sample may be obtained.

The regression analysis used to determine the coefficients of the prediction model may be based on linear regression techniques or non-linear regression techniques. It will be noted that even while the coefficients of regression may be determined using linear regression, the complete yield profile or refining characteristic profile obtained therefrom may not necessarily be linear in nature, and hence the plot obtained may not be linear.

As would be known to a person skilled in the art, and, for the sake of clarity and better understanding, the distillates and residues as obtained from the distillation of any given oil sample, with respect to different temperature ranges are listed below in table 1.

TABLE 1

Different products as obtained for increasing temperature ranges.

| | |
|---|---|
| Initial Boiling Point (IBP) - 140 degree Celsius | Naphtha |
| 140 degrees to 240 degrees Celsius | Kerosene |
| 240 degrees to 360 degrees Celsius | Gas Oil |

TABLE 1-continued

Different products as obtained for increasing temperature ranges.

| | |
|---|---|
| 360 degrees and above | Atmospheric Residue |
| 360 degree Celsius to 565 degree Celsius | Vacuum Gas Oil |
| 565 degree Celsius and above | Vacuum Residue |

In another embodiment of the present subject matter, the prediction model may be used for the prediction of hydrogen consumption in hydro processing and intermediate refinery distillate streams. The prediction of hydrogen consumption may be based on specific refinery configuration and assumptions. Further, the processing costs may include cost of the hydrogen consumed for hydro processing of the gas oils and cost of evacuating residues, such as fuel oil by means of cutter stocks. Cutter stocks are petroleum stocks which are used to reduce the viscosity of a heavier crude oil by dilution.

In yet another embodiment of the present subject matter, the prediction model may be used for the prediction of the ranking of the given oil sample. The prediction of the ranking of the oil sample may be based on the crude oil price differential and refinery processing cost differential. The information regarding the predicted ranking of the oil sample is further processed to determine refinery processing costs based on the actual configuration of refinery and thus crude oils can be ranked. This is based on the net differential of discounts on crude oils due to qualities of given crude oils with respect to a reference crude oil, such as, Brent crude oil; and additional refinery processing costs.

In yet another embodiment of the present subject matter, the prediction of refining characteristics may also include prediction of at least one characteristic selected from Volume Average Boiling Point (VABP), Universal Oil Characterization factor (UOP-k), mean average boiling point (MeABP), kinematic viscosity, asphaltenes, pour point, mercaptan, and molecular weight of the oil sample. The Universal Oil Characterization factor determines the amount of aromatics and paraffin in an oil sample. The Volume Average Boiling Point is indicative of the average boiling point of an oil sample as a whole. In an implementation, the VABP, UOP-k, MeABP and the molecular weight of the oil sample may be inter related. In another implementation, the VABP, UOP-k, MeABP and molecular weight may collectively be used to predict the aromatic, naphthenic and paraffinic nature of the oil sample, which may be further used to select the oil sample based on the refinery configurations.

In another embodiment, the prediction of refining characteristics may further include prediction of production of at least one of bitumen, Fuel Oil (FO) or Low Sulphur Heavy Stock (LSHS) from the oil sample. The predicted production of bitumen, FO and LSHS is indicative of the quality and ease of processing of the oil sample, as will be understood by a person skilled in the art.

The determination of the refining characteristics based on the methods of the present subject matter are easier, less time consuming and more accurate than the conventional methods. Moreover, use of at least one of Conradson Carbon Residue (CCR) content, Ramsbottom Carbon Residue (RCR) and Micro Carbon Residue (MCR) for prediction of refining characteristics helps in determining more accurately the yield profile, especially for vacuum gas oil and vacuum residue, which in turn helps in better pricing and in planning and optimization of refinery operations for greater profitability.

FIG. 1 illustrates various components of a characteristic prediction system 100, according to an embodiment of the present subject matter. The characteristic prediction system 100 includes one or more processor(s) 104, one or more interfaces 106 and a memory, such as a memory 102, coupled to the processor(s) 104. It will be understood that the characteristic prediction system 100 may be implemented as any suitable computing system known in the art, such as a desktop, a laptop, a server, and the like.

The interfaces 106 may include a variety of software and hardware interfaces, for example, interfaces for peripheral device(s), such as a keyboard, a mouse, an external memory, and a printer. The interfaces 106 can facilitate multiple communications within a wide variety of networks and protocol types, including wired networks, for example, local area network (LAN), cable, etc., and wireless networks, such as Wireless LAN (WLAN), cellular, or satellite. For the purpose, the interfaces 106 may include one or more ports for connecting a number of devices to each other or to another computing system.

The processor 104 can be a single processing unit or a number of units, all of which could include multiple computing units. The processor 104 may be implemented as one or more microprocessors, microcomputers, microcontrollers, digital signal processors, central processing units, state machines, logic circuitries, and/or any devices that manipulate signals based on operational instructions. Among other capabilities, the processor 104 is configured to fetch and execute computer-readable instructions and data stored in the memory 102.

The functions of the various elements shown in the figures, including any functional blocks labeled as "processor(s)", may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non volatile storage.

The memory 102 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. The memory 102 includes module(s) 108 and data 116. The modules 108, amongst other things, include routines, programs, objects, components, data structures, etc., which perform particular tasks or implement particular abstract data types.

The data 116 serves, amongst other things, as a repository for storing data processed, received and generated by one or more of the modules 108. The data 116 may include data related to samples of known crude oils, i.e., crude oil data 118, regression data 120 and other data 122. The modules 108 further include, for example, a receiving module 110, a regression module 112, and a prediction module 114. The data 116 includes data generated as a result of the execution of one or more modules.

In operation and to generate a prediction model, according to an implementation of the present subject matter, the receiving module 110 of the characteristic prediction system 100 receives physical properties, including at least at least one of Conradson Carbon Residue (CCR) content, Ramsbottom Carbon Residue (RCR) and Micro Carbon Residue (MCR), for a plurality of known oil samples. The measurement of physical properties for these known oil samples may be done by industry specified protocol methods such as shown in Table 2.

TABLE 2

Industrial Methods for measurement of Physical properties.

| Sample | Analyses Details | Method |
| --- | --- | --- |
| Any given oil sample | Density, Specific Gravity and/or API Gravity | ASTM D4052 |
| | Sulphur | ASTM D2622, D4294, D5453 |
| | Mercaptan | ASTM D3227 |
| | Kinematic Viscosity (KV) | ASTM D445 |
| | Pour Point | ASTM D97, D5853, D5950 |
| | Acidity | ASTM D664 |
| | Fe, V, Ni, Na, Cu, Zn | ICP-AES |
| | Total Nitrogen | ASTM D4629 |
| | Basic Nitrogen | UOP 269 |
| | Yields (% wt & % vol) | ASTM D2892 and D5236 |
| | ASTM Distillation | ASTM D86 |
| | Freezing Point | ASTM D2386 |
| | Conradson Carbon Residue (CCR) | ASTM D189 |
| | Micro Carbon Residue (MCR) | ASTM D4530 |
| | Ramsbottom Carbon Residue (RCR) | ASTM D524 |
| | Asphaltenes | ASTM D6560 |
| | Salt | ASTM D3230 |
| | RVP | ASTM D323 |
| | Aniline point | ASTM D611 |

As depicted in table 2, industrial protocol methods for measurement of physical properties for any oil sample are known. In accordance with the present subject matter, the physical properties measured include at least one of CCR content, RCR and MCR along with one or more other physical properties, such as Sulphur content, Carbon content, Hydrogen content, Nitrogen content, API gravity, Pour point, Viscosity, Saturates, Aromatics, Resins, Asphaltenes and the like.

This data may be stored in a crude oil database 124 for further use in the prediction of the refining characteristics for the oil sample. The regression module 112 processes this data for calculation of regression coefficients for the prediction model that can be used to predict one or more of the refining characteristics of the oil sample. The refining characteristics are also referred to as characteristics hereinafter.

In one implementation of the present subject matter, the regression module 112 uses characteristics data for multiple known oil samples to calculate the coefficients of regression. In one implementation, the calculation of the coefficients of regression is based on a method of linear regression. These coefficients are then used to generate prediction models that are used to predict the characteristics of the given oil sample. It may be noted that, these measured physical properties include at least one of CCR content, RCR and MCR. Additionally, one or more physical properties selected from the group of Sulphur content, Carbon content, Hydrogen content, Nitrogen content, API gravity, Mercaptan value, Kinematic viscosity, Pour point, Ramsbottm Carbon Residue (RCR), Micro Carbon Residue (MCR), Saturates, Aromatics, Resins, and Asphaltenes can be used. It will be understood that other methods of non-linear regression, such as polynomial regression and logarithmic regression, may also be used for determination of the regression coefficients.

Further, the prediction module 114 can predict the characteristics of the oil sample based on the coefficients of regression and prediction model generated by the regression module 112. The characteristics may include one or more of distillate and residue yield profile, hydrogen consumption in hydro processing and intermediate refinery distillate streams, pricing parameter and ranking of crude oils on the basis of net margins offered over crude cost differentials, VABP and UOPK factors, Mean Average Boiling Point (MeABP) and molecular weight. Further, the prediction of characteristics may also include prediction of residue potential for determining at least one of bitumen, Fuel Oil (FO) or Low Sulphur Heavy Stock (LSHS) production. It will be understood that multiple prediction models may be generated for the prediction of different characteristics. Also, based on the predicted characteristics, further decisions can be taken, for example, regarding optimum crude blends, efficient resource utilization in the refinery, and the like.

The crude oil database 124 may be used to store the physical properties as obtained by the receiving module 110. The crude oil database 124 may also be used to store the measured coefficients of regression for plurality of known samples and their measured physical properties. Thus, it will be understood that the crude oil database 124 may be used for storing any relevant data relating to the characteristic prediction system 100.

Figure 2:
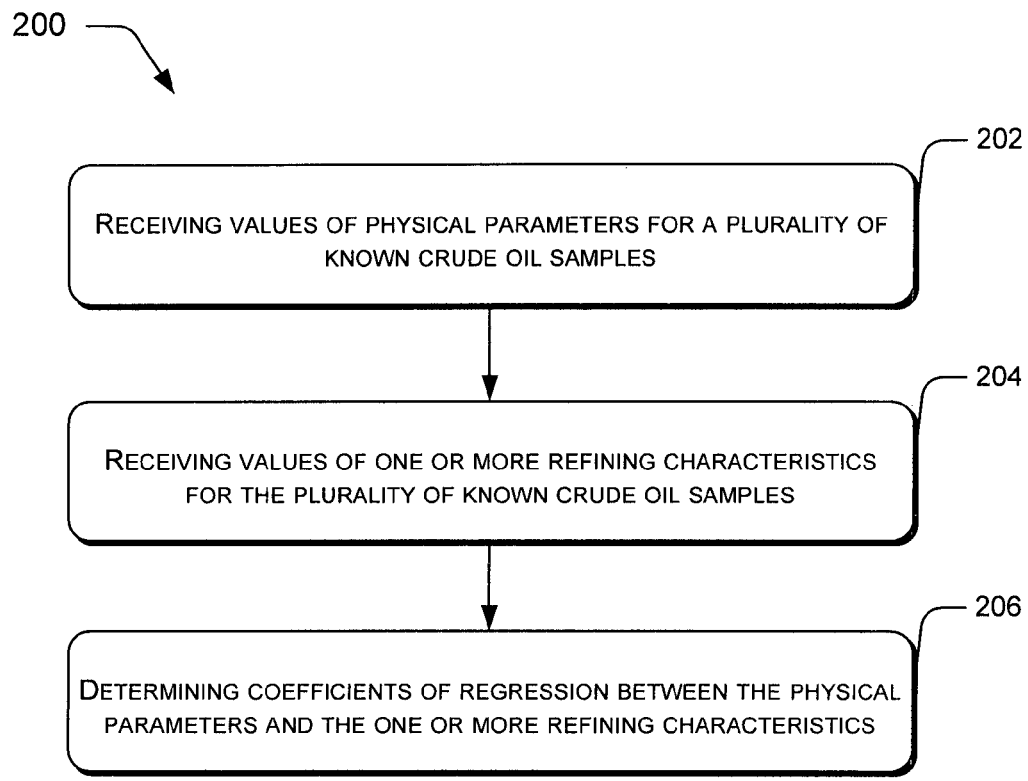
FIG. 2 illustrates a method to determine coefficients of regression of a prediction model, in accordance with an implementation of the present subject matter.
Figure 3:
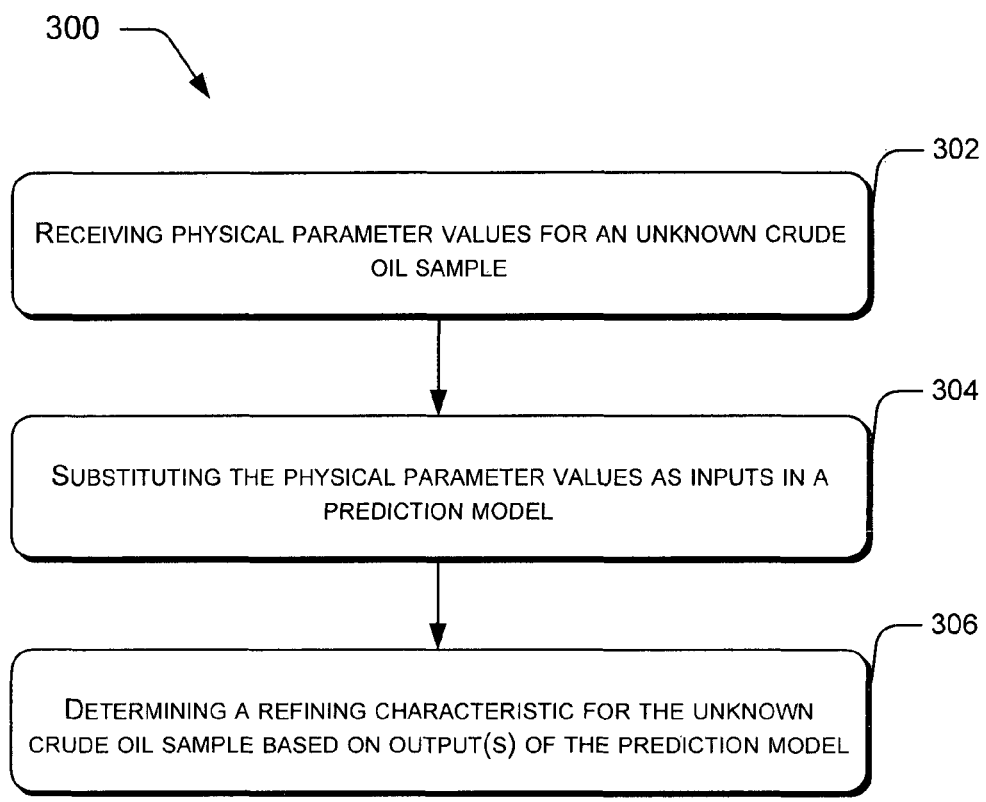
FIG. 3 illustrates a method to predict refining characteristics based on the prediction model, in accordance with an implementation of the present subject matter.

FIG. 2 illustrates an exemplary method 200 for calculating coefficients of regression for known crude oil samples, in accordance with an implementation of the present subject matter. FIG. 3 illustrates an exemplary method 300 for prediction of characteristics for any given oil sample, in accordance with an implementation of the present subject matter. For explanation, the concepts of calculation of coefficients of regression and prediction of characteristics are described with reference to the characteristic prediction system 100.

The exemplary methods may be described in the general context of computer executable instructions. Generally, computer executable instructions can include routines, programs, objects, components, data structures, procedures, modules, functions, etc., that perform particular functions or implement particular abstract data types. The methods may also be practiced in a distributed computing environment where functions are performed by remote processing devices that are linked through a communications network. In a distributed computing environment, computer executable instructions may be located in both local and remote computer storage media, including memory storage devices.

The order in which the method blocks are described is not intended to be construed as a limitation, and any number of the described method blocks can be combined in any order to implement the method, or an alternative method. Additionally, individual blocks may be deleted from the methods without departing from the spirit and scope of the subject matter described herein. Furthermore, the methods can be implemented in any suitable hardware, software, firmware, or combination thereof. The methods are explained with reference to a characteristic prediction system 100, however, it will be understood that the methods 200 and 300 can be implemented for a plurality of characteristic prediction systems also.

At block 202, values of a plurality of physical parameters are received for known oil samples. For example, the receiving module 110 may receive measured values for a plurality of physical properties like Conradson Carbon Residue (CCR) content, Carbon content, Hydrogen content, Nitrogen content, API gravity, Sulphur content, and the like. It may also receive other physical properties, such as boiling points, pour points, viscosities, RCR, MCR, asphaltenes, mercaptan and the like, for the known oil samples.

As block 204, one or more refining characteristics are received for the known oil samples. The refining characteristics are then saved in the crude oil database 124 and may be retrieved, for example, by the receiving module 110. The plurality of physical properties and the corresponding refining characteristics are hence available for further processing.

At block 206, a set of coefficients of regression are determined in order to generate the prediction model between the physical parameters and the one or more refining characteristics. In one implementation, the set of coefficients of regression are calculated based on linear regression, for example, by the regression module 112.

The set of coefficients of regression are calculated from multiple linear regression equations, based on the refining characteristics and physical properties of multiple known oil samples. Regression analysis is a well known statistical technique for determining coefficients that correlate the value of a variable with values of one or more known parameters. Using such regression techniques, coefficients can be determined to correlate a refining variable, such as yield of a distillate fraction, with one or more physical parameters. These coefficients can be then used to predict characteristics of any unknown or given oil sample, which may include crude oils, crude oil blends, and hydrocarbon mixtures. In one implementation, the coefficients of regression are also stored in the crude oil database 124 for further processing.

Moving now to FIG. 3 and exemplary method 300 for prediction of characteristics for any given oil sample, in accordance with an implementation of the present subject matter.

At block 302, a plurality of physical parameters values including at least one of CCR, RCR and MCR is received for an oil sample for which one or more refining characteristics are to be predicted. The oil sample may be any given unknown crude oil, unknown blend or synthetic crude oils or any unknown hydrocarbon. The plurality of physical property values is calculated for the oil sample based on the industrial protocol methods, as mentioned above in Table 2.

At block 304, the measured physical properties, are used as inputs in the prediction model. The prediction model is generated using coefficients of regression, wherein, in one implementation, the calculation of the coefficients of regression is based on linear regression, as described earlier. In one example, the prediction model may be generated by the regression module 112. It may be noted, that multiple prediction models may be formed for different characteristics to be predicted for any given oil sample. Thus, any number of characteristics may be predicted for the oil sample, based on the generated coefficients of regression.

At block 306, one or more refining characteristics are calculated from the various prediction models. The refining characteristics are obtained as outputs from the prediction models. In one example, the prediction module 114 determines the refining characteristics based on the prediction models. The outputs correspond to the different characteristics including, distillate and residue profile, probable yields and quality, blends, pricing, processability, hydrogen consumption in hydro processing, residue-potential, secondary processing, and the like of the oil sample.

Figure 4A:
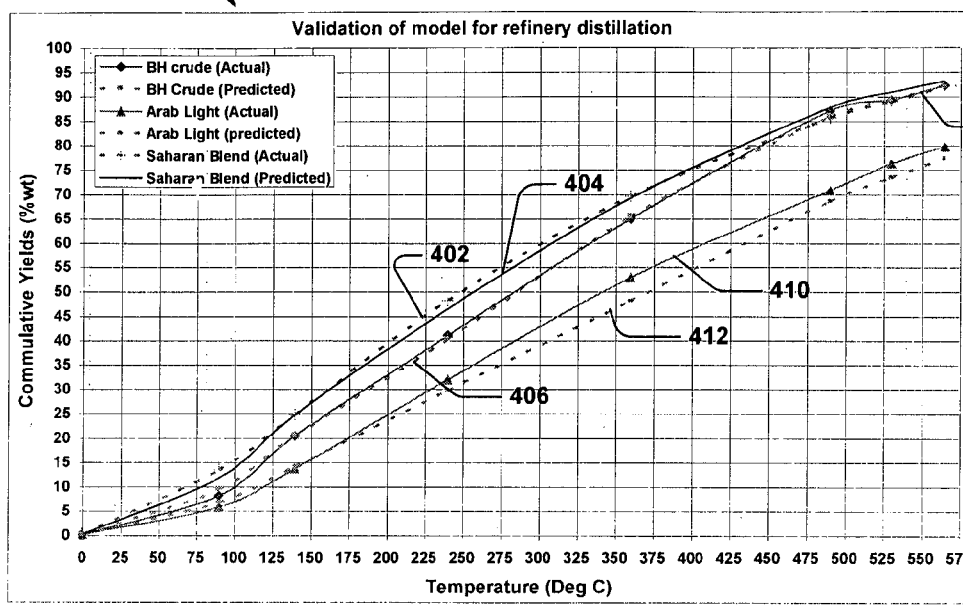
FIG. 4(a) illustrates a graphical representation of validation of the prediction model for refinery distillation profile, in accordance with an implementation of the present subject matter.
Figure 4B:
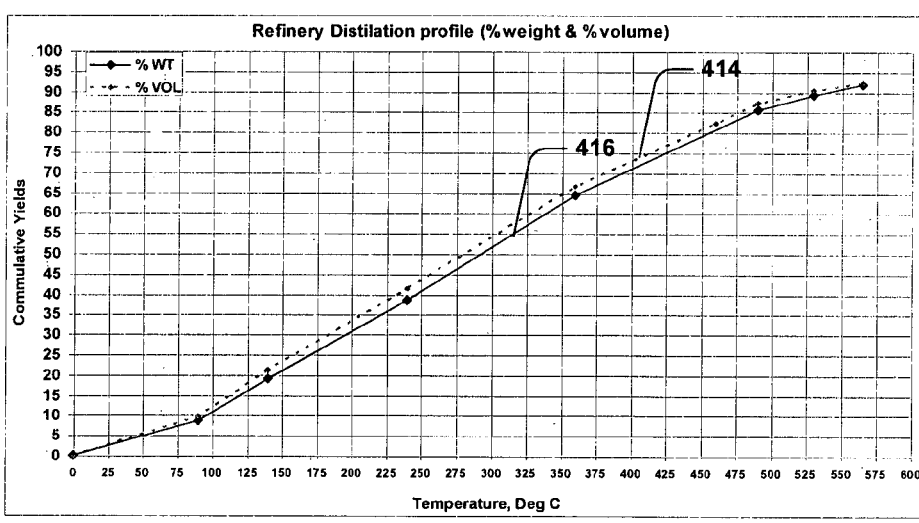
FIG. 4(b) illustrates a plot of refinery distillation profile of the given oil sample, in accordance with an implementation of the present subject matter.

FIG. 4(a) and FIG. 4(b) illustrate the validation plots for the prediction model as generated using the coefficients of regression for known oil samples. This validation is done by predicting the distillate and residue yield profile for three known crude oil samples viz., Bombay High (source: India), Saharan Blend (source: Algeria) and Arab Light (source: Saudi Arabia). Values of the measured physical properties for these crude oil samples are depicted in Table 3.

TABLE 3

Values of physical properties of crude oils

| Properties | Units | BH crude | Arab Light | Saharan Blend |
|---|---|---|---|---|
| Origin | — | India | Saudi Arabia | Algeria |
| API Gravity | — | 38.94 | 32.93 | 42.35 |
| Total Sulpriur | % wt | 0.158 | 1.754 | 0.163 |
| RVP at 38° C. | kg/cm2 | 0.310 | 0.358 | 0.380 |
| Kinematic Viscosity, 40° C. | cSt | 2.544 | 7.959 | 2.18 |
| Pour Point | ° C. | 12.00 | INA | −39 |
| TAN | mg KOH/gm | 0.06 | 0.09 | 0.18 |
| CCR | % wt | 1.250 | 4.476 | 1.080 |
| Asphaltenes | % wt | 0.155 | 1.687 | 0.047 |
| C | % wt | 86.32 | 85.6 | 85.35 |
| H | % wt | 13.52 | 12.64 | 13.82 |
| N | Ppm | 252 | 887 | 357 |
| Vanadium | Ppm | 1.6 | 13.00 | <0.5 |
| Nickel | | 1.4 | 7.00 | 1.3 |
| Copper | | 0.196 | 5.8 | 0.1 |
| Iron | | 4.08 | 17.00 | 19.5 |

As depicted in table 3 values of the physical properties for the three crude oils, taken for validation, are determined. These properties include API gravity, Sulphur content (in weight %), CCR content (in weight %) and Asphaltenes content (in weight %). More physical properties, such as RCR, MCR, Pour point, Viscosity, Freeze point, and the like may also be listed down.

As shown in FIG. 4(a), the validation of model is based on a graph 400(a) between the cumulative yields in weight percent of the crude oils and different temperature ranges in degree Celsius. The predicted relation between cumulative yields and temperature ranges for the Saharan Blend crude are as depicted by the curve 402 of the graph. The actual relation between the cumulative yields of the Saharan Blend crude with respect to temperature ranges is as depicted by curve 404. As is clearly evident from the two curves, the predicted value of the cumulative yields is very close to the actual cumulative yield values.

Similarly, the curve 406 depicts the relation as predicted between the cumulative yields and the temperature ranges for Bombay High (BH) crude and the curve 408 depicts the actual relation between cumulative yields and temperature ranges for the BH crude. Further, predicted relation between cumulative yields in weight percentage and temperature ranges for the Saharan Blend crude oil is as depicted in curve 410, whereas the actual relation between the cumulative yield and temperature ranges is as depicted in curve 412. As is clearly evident from the graph 400(a), the predicted relation of the cumulative yields and the temperature ranges is very close to the actual relation. Hence, the prediction model is validated with an accuracy ranging between 92-97%.

A plot 400(b) of the refinery distillation profile is depicted in the FIG. 4(b). The plot is obtained between cumulative yields and the temperature for both the weight percentage and volume percentage. The plot 400(b) clearly depicts that the prediction model generated for the prediction of distillate and residue yield profile can predict the yields both in the form of volume percentage (as depicted by curve 414) as well as that of weight percentage (as depicted by curve 416).

In an embodiment of the present subject matter, plot 400(*b*) may also be used for the prediction of other physical parameters or refining characteristics, including at least one of Volume Average Boiling Point (VABP), Universal Oil Characterization factor (UOP-k), mean average boiling point (MeABP), molecular weight, kinematic viscosity, asphaltenes, pour point, and mercaptan content of the oil sample. In an implementation, the VABP, UOP-k, MeABP and molecular weight may collectively be used to predict the aromatic, naphthenic and paraffinic nature of the oil sample, which may be further used to select an oil sample based on the refinery configurations.

Figure 5A:
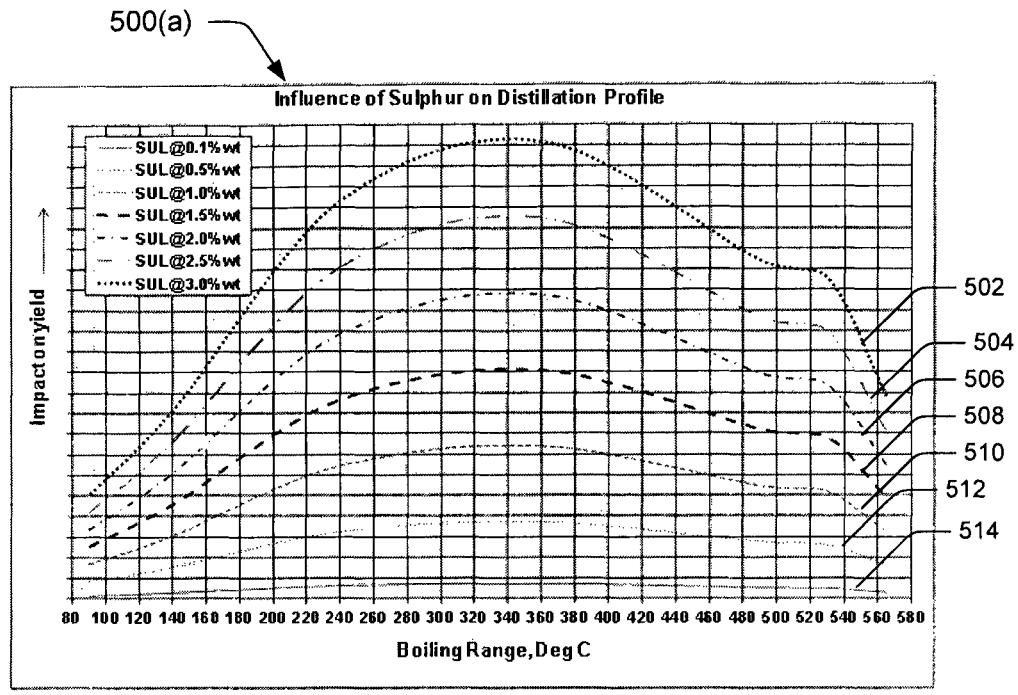
FIG. 5(a) illustrates an influence of Sulphur on the refinery distillation profile of the given oil sample, in accordance with an implementation of the present subject matter.
Figure 5B:
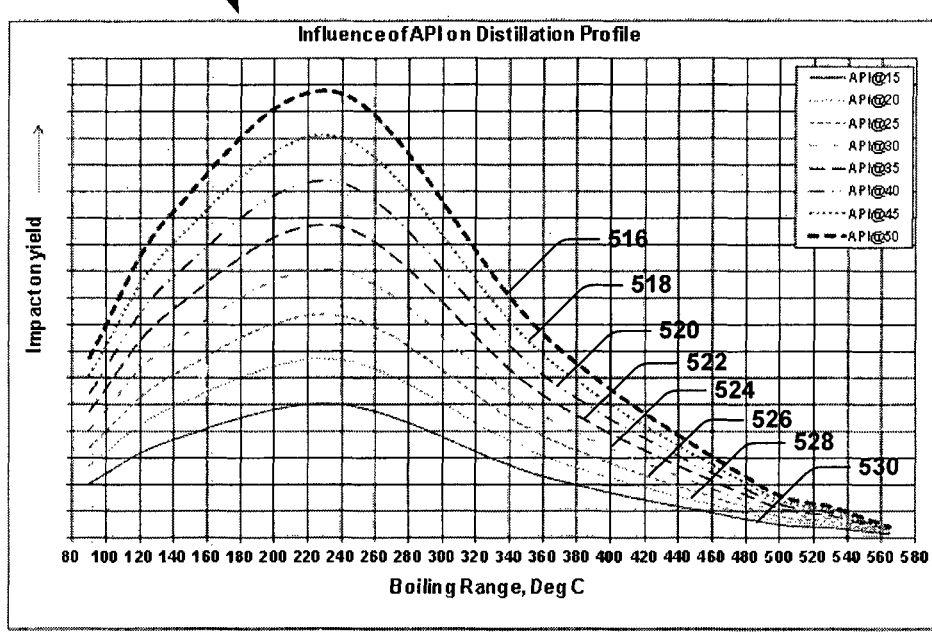
FIG. 5(b) illustrates an influence of API gravity on the refinery distillation profile of the given oil sample, in accordance with an implementation of the present subject matter.

FIGS. 5(*a*), 5(*b*), and 6(*a*) depict the impact of different physical properties on the residue and distillate yield profile. It will be understood by a person skilled in the art, that similar influences of the same or other physical properties on the same or other refining characteristics, as described above, may also be depicted.

FIG. 5(*a*) depicts the impact of the Sulphur content on the distillate and residue profile, collectively referred to as the distillation profile, for any given oil sample via a graph 500(*a*). The slopes of curves 502-514 depict how the impact on yield varies with temperature in degree Celsius as the sulphur content changes for six different unknown oil samples. The Sulphur content in the samples varies from 0.1% by weight to 3% by weight as depicted in the graph 500(*a*). As is evident from the graph 500(*a*), as the value of Sulphur content in weight percentage increases, the impact on yield has a definite increase for a temperature range of about 80 degree Celsius to about 360 degree Celsius. Also, after a temperature of about 530 degree Celsius there is a considerable drop in the yield due to negative impact on the yield as denoted by the negative slope of the curves. Using table 1 and the graph 500(*a*), influence of Sulphur content on the yield of the distillates and residues may easily be understood. For example, for the graph 500(*a*), it can be understood that the Sulphur content will cause an increase in the yield percentage for products falling in the temperature range of Initial Boiling Point (IBP) (here 80 degree Celsius) to a temperature of 360 degree Celsius. Hence, there will be an increase in the yield of Naphtha, Kerosene and Gas Oil for an increase in Sulphur for the oil sample. However, yield of Vacuum Residue, which is obtained for a temperature range of 565 degrees and above, will decrease for an increase in the Sulphur content of the oil sample.

FIG. 5(*b*) depicts the impact of API gravity on the distillation profile for the oil sample via a graph 500(*b*). As shown by the slope of the curves 516 to 530, as the value of API gravity increases for the oil sample, the impact on the yield for the temperature range of IBP to a temperature range of about 240 degree Celsius increases by a noticeable amount. That is, as the API gravity increases for the oil sample, there is an increase in the yield of Naphtha and Kerosene for the oil sample. As is also evident from the graph 500(*b*), there is a noticeable decrease in yield in the temperature ranges of about 240 degree Celsius to about 560 degree Celsius. Hence, it may be easily understood that as the API gravity for the oil sample increases there is a decrease in the yields of Gas oil and Vacuum Gas Oil. Also, as seen from the graph 500(*b*) the amount of Vacuum residue does not change significantly with a change in the API gravity for the oil sample.

Figure 6A:
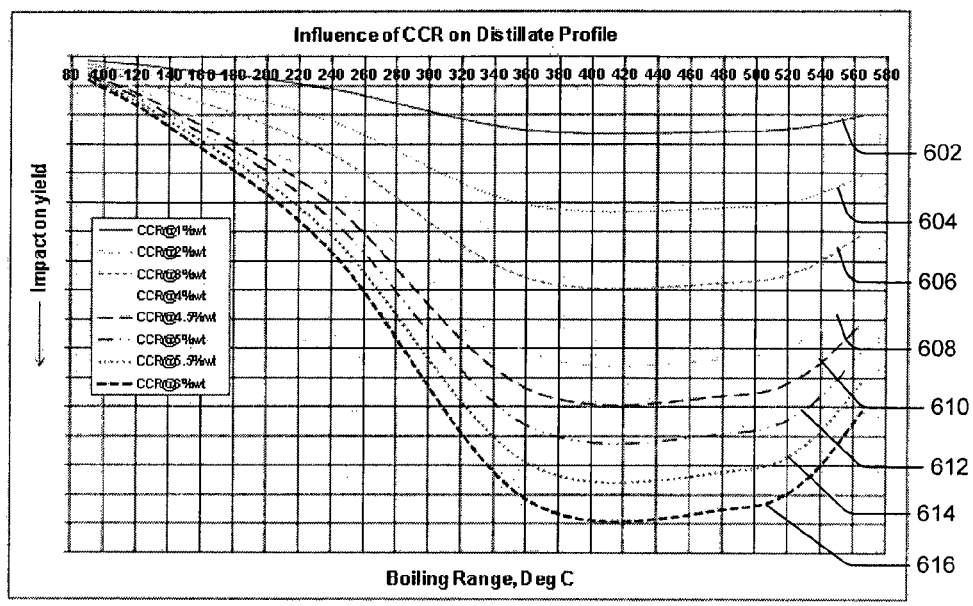
FIG. 6(a) illustrates an influence of CCR on the refinery distillation profile of the given oil sample, in accordance with an implementation of the present subject matter.
Figure 6B:
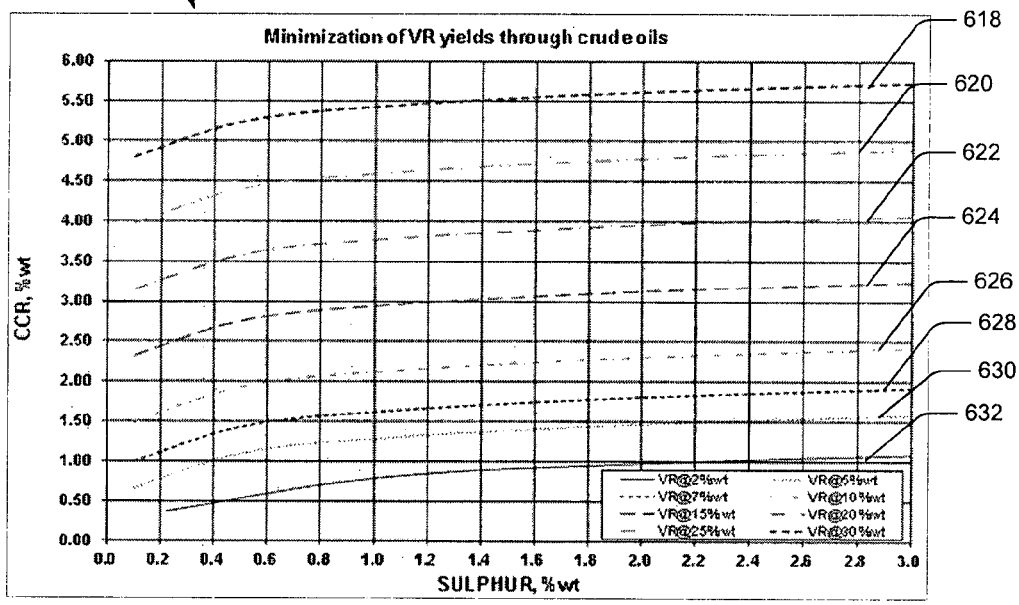
FIG. 6(b) illustrates a graph depicting minimization of Vacuum Residue based on physical properties of the given oil sample, in accordance with an implementation of the present subject matter.

FIG. 6(*a*) depicts the influence of CCR content on the distillation profile in the form of the curves 602-616 in the graph 600(*a*). As is evident from the slopes of the curves 602-616, for a temperature range of IBP to about 240 degree Celsius there is a negative impact on yield for an increase in CCR content, i.e., the amount of Naphtha and Kerosene produced decreases slightly for an increase in the CCR content. Further, for a temperature range of about 240 degree Celsius to about 360 degree Celsius, there is a greater negative impact on the yields, i.e., the amount of Gas Oil production would decrease substantially for an increase in CCR content. Furthermore, the impact on yield of Vacuum Gas Oil is slightly positive for an increase in the value of CCR content as depicted from the section of the graph 600(*a*) between temperature ranges of about 360 degree Celsius to about 560 degree Celsius. Similarly, it can be seen that there is a considerable positive impact on yield of Vacuum Residue for an increase in the value of CCR content for the oil sample, as is evident from the graph 600(*a*).

Thus, while Sulphur content and API gravity show a positive impact on the yields of lighter fractions and negative impact on yields of heavier fractions, carbon content shows a negative impact on the yields of the lighter fractions and positive impact on yields of heavier fractions, as can be seen from graphs 500(*a*), 500(*b*) and 600(*a*). Moreover, the effect of carbon content is more pronounced on the yields obtained above 240 degree Celsius. Hence, by including a measure of carbon content, such as CCR, the prediction model becomes more accurate.

FIG. 6(*b*) depicts the combined effect of Sulphur content and CCR on Vacuum Residue for a given oil sample, through the curves 618-632 in the graph 600(*b*). Vacuum Residue is the end product obtained in the process of Vacuum Distillation and hence, it affects the refinery profitability. Therefore, the refineries may want to select an oil sample that produces minimum amount of Vacuum Residue in order to meet refinery constraints and for better refinery profitability. The graph 600(*b*) is plotted between the amount of Sulphur content in weight percentage and the CCR content in weight percentage. The graph 600(*b*) can be used in order to select any oil sample for obtaining Vacuum Residue less than a maximum acceptable amount as per the refinery constraints.

Figure 7:
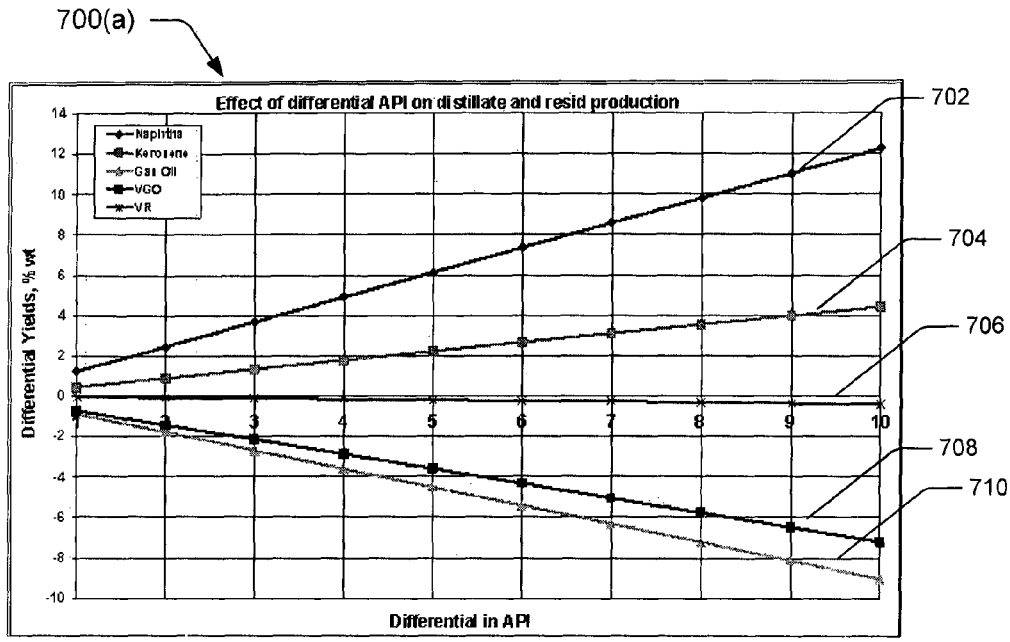
FIG. 7(a) illustrates an effect of differential API on the refinery distillation profile of the given oil sample, in accordance with an implementation of the present subject matter.
FIG. 7(b) illustrates an effect of differential Sulphur on the refinery distillation profile of the given oil sample, in accordance with an implementation of the present subject matter.
Figure 7:
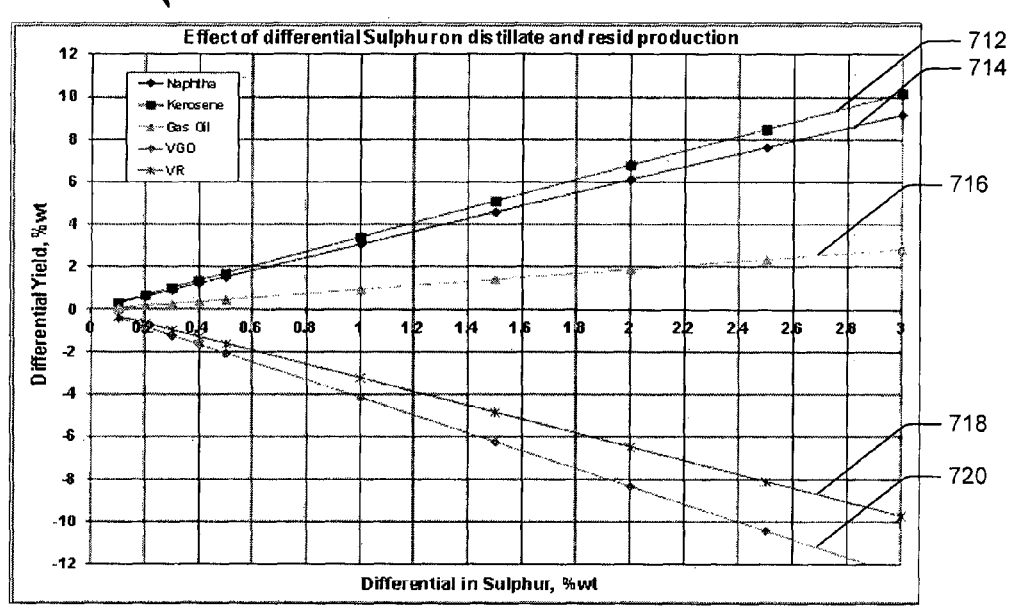

FIGS. 7(*a*), 7(*b*) and 8 depict the influence of three physical properties i.e. API gravity, Sulphur content and CCR content on the yield of specific distillation products for the oil sample. It may be noted by a person skilled in the art that such graphs may be obtained for other physical properties' influence on the distillation products as well.

FIG. 7(*a*) depicts the influence of API gravity for different distillates and residues for the oil sample. As depicted, the graph 700(*a*) shows a relation between the differential yields in weight percentage and the API gravity for different distillation products. As depicted by 702 and 704 respectively, the yields of Naphtha and Kerosene increase with an increase in the API gravity of the oil sample. Similarly, 708 and 710 respectively show a decrease in the yield of Vacuum Gas Oil and Gas Oil for an increase in the value of API gravity. Also, the yield of Vacuum Residue is almost constant for an increase in the API gravity, as is shown by 706. This is inline with the impact on yield of API gravity as depicted in FIG. 5(*b*).

FIG. 7(*b*) depicts the influence of Sulphur content for different distillates and residues for the oil sample. The graph 700(*b*) shows a relation between the differential yields in weight percentage and the Sulphur content for different distillation products. As depicted by 712, 714 and 716 respectively, the yields of Kerosene, Naphtha and Gas Oil increase with an increase in the Sulphur content of the oil sample. Similarly, 718 and 720 respectively show a decrease in the yield of Vacuum Residue and Vacuum Gas Oil for an increase in the value of Sulphur. This is inline with the impact on yield of Sulphur content as depicted in FIG. 5(a).

Figure 8:
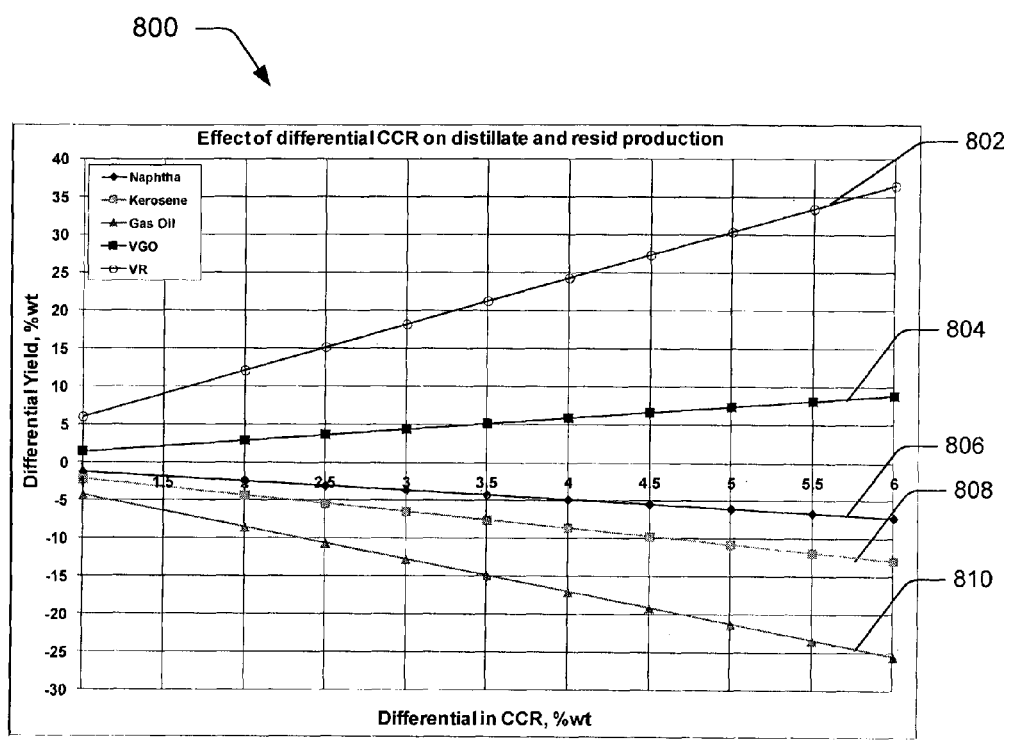
FIG. 8 illustrates an effect of differential CCR on the refinery distillation profile of the given oil sample, in accordance with an implementation of the present subject matter.

FIG. 8 depicts the influence of CCR content on yields of different distillates and residues through a graph 800. It may be shown that the yields of Vacuum Residue and Vacuum Gas oil increase with an increase in CCR content. This is shown by 802 and 804 respectively. On a similar note, it is shown by curves 806, 808 and 810 respectively, that there is a decrease in the yields of Naphtha, Kerosene and Gas Oil for an increase in the value of CCR content for any oil sample. This is inline with the impact on yield of CCR as depicted in FIG. 6(a).

Thus, from the various graphs discussed above, it can be seen that the distillation profiles can be correlated with the physical parameters. In one example, the predicted yields may be directly proportional to the physical parameters. However, it will be understood that the proportionality constants may be either positive or negative, thereby indicating a positive correlation or negative correlation, respectively.

Further, from FIGS. 7(a), 7(b) and 8, it can be inferred that the increase in Naphtha and Kerosene production is positively correlated to API gravity and Sulphur content and negatively correlated to Carbon Residue content. Also, the increase in Vacuum Gas Oil and Atmospheric Residue production is positively correlated to Carbon Residue content and is negatively correlated to API gravity and Sulphur content. Furthermore, the increase in Gas Oil production is positively correlated to Sulphur content and negatively correlated to API gravity and Carbon Residue content. Also, the increase in Vacuum Residue production is positively correlated to Carbon Residue content, negatively correlated to Sulphur content, and is negligibly dependent on API gravity.

As mentioned above, the characteristic prediction system 100 and methods 200 and 300 can be used for predicting any refining characteristic. In an embodiment of the present subject matter, method(s) and system(s) for predicting refinery processing cost as the refining characteristic has also been described. The refinery processing costs may include cost of resources such as hydrogen, which is consumed in the hydro processing of gas oils derived from the oil sample and the cost of evacuating residue by means of cutter stocks (based on specific refinery configurations and assumptions). The method of predicting the refinery processing costs may include development of a prediction model based on regression as described with reference to method 200. The method may further include determining the physical properties of the oil sample and predicting the refining characteristics based on the developed prediction model as described with reference to method 300. The determination of the physical properties of the oil sample includes determining at least one of CCR content, RCR and MCR.

Figure 9:
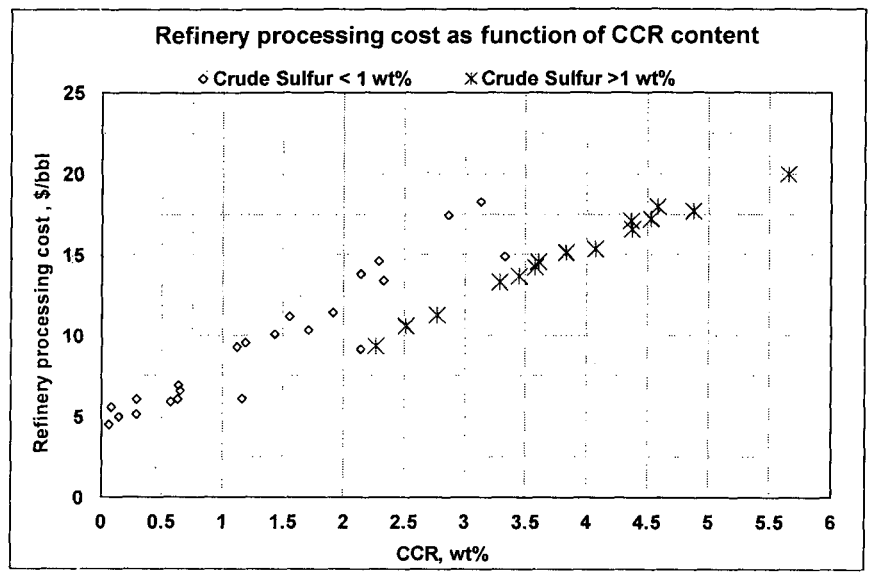
FIG. 9 (a) illustrates a graph showing refinery processing cost as function of CCR content of the given oil sample, in accordance with an implementation of the present subject matter.
Figure 9:
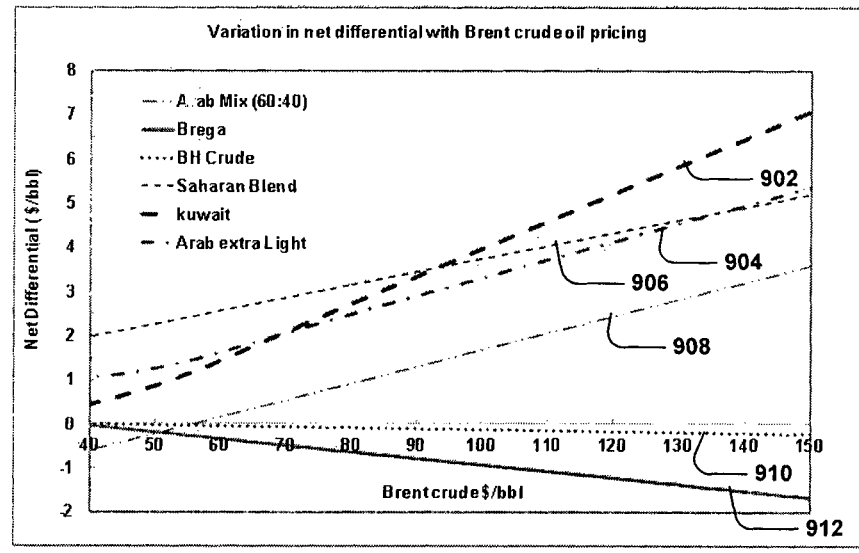

FIG. 9 (a) depicts the influence of CCR content on the refinery processing cost for low Sulphur (S<1 wt %) oil samples and high Sulphur (S>1 wt %) oil samples. As previously described, the refinery processing costs include costs for hydro processing and residue evacuation as fuel oils at cheaper prices for refineries where upgradation facilities are unavailable. While evacuating residues as fuel oil, valuable distillates are also being used as cutter stocks, and hence downgraded in the process. Thus, predicting refinery costs may be used for selecting oil samples having lesser processing costs. As depicted in the graph 900(a), for the low Sulphur oil sample, the refinery processing cost (in dollars/barrel) increases for an increase in the CCR content. Similarly, as shown, for high Sulphur oil samples as the CCR content increases, the refinery processing cost increases. Further, initial refinery processing cost for a low Sulphur oil sample is lesser than that for a high Sulphur oil sample. However, if the CCR content of the low sulphur oil sample is high, i.e. of the order of 2 wt % or more, then the refinery processing cost of the high CCR and low sulphur oil becomes equivalent to the initial refinery processing cost of high sulphur oil. Thus, use of CCR content helps in more accurately predicting the refinery processing cost.

In yet another embodiment of the present subject matter, method(s) and system(s) for ranking of crude oils as the refining characteristic, based on scenarios of crude oil quality and pricing, yield profile, specific refinery constraints and configuration has also been described. In an implementation, the ranking of the crude oils may be predicted on the basis of crude price differential and refinery processing cost differential. The crude price differential may be estimated by calculating the differential of the price of the crude oil sample with respect to the price of a standard crude oil, such as the Brent Crude oil, for a barrel. Further, the refinery processing cost differential may be estimated by calculating the refinery processing cost differential of the crude oil with respect to the refinery processing cost of the standard crude oil for a specific refinery. The method may further include predicting the ranking of the crude oil based on the crude oil price differential and the processing cost differential. Furthermore, the method may include determining the physical properties of the oil sample and predicting the refining characteristics based on the developed prediction model. The determination of the physical properties of the oil sample includes determining at least Conradson Carbon Residue (CCR) content.

FIG. 9 (b) depicts the ranking of crude oils vis-à-vis Brent crude price variations for given crude oils, e.g., Arab Mix (source: Saudi Arabia), Brega (source: Libya), BH crude (source: India), Saharan Blend (source: Algeria) and Kuwait (source: Kuwait). The crude price variations are due to variation in net differential discounts, i.e., discounts due to crude oil qualities and refinery processing cost, for various Brent crude price scenarios. As shown in the plot 900(b) the cross over in net margin (ranking of crude oils) is evident due to variation in Brent crude oil price. Thus, measurement of physical properties sample, including determining at least CCR content, RCR and MCR, can be used for the ranking of crude oils for net margins at refineries with varying Brent crude pricing. The ranking of crude oils can be then used for selection of appropriate blend of crude oil.

Figure 10:
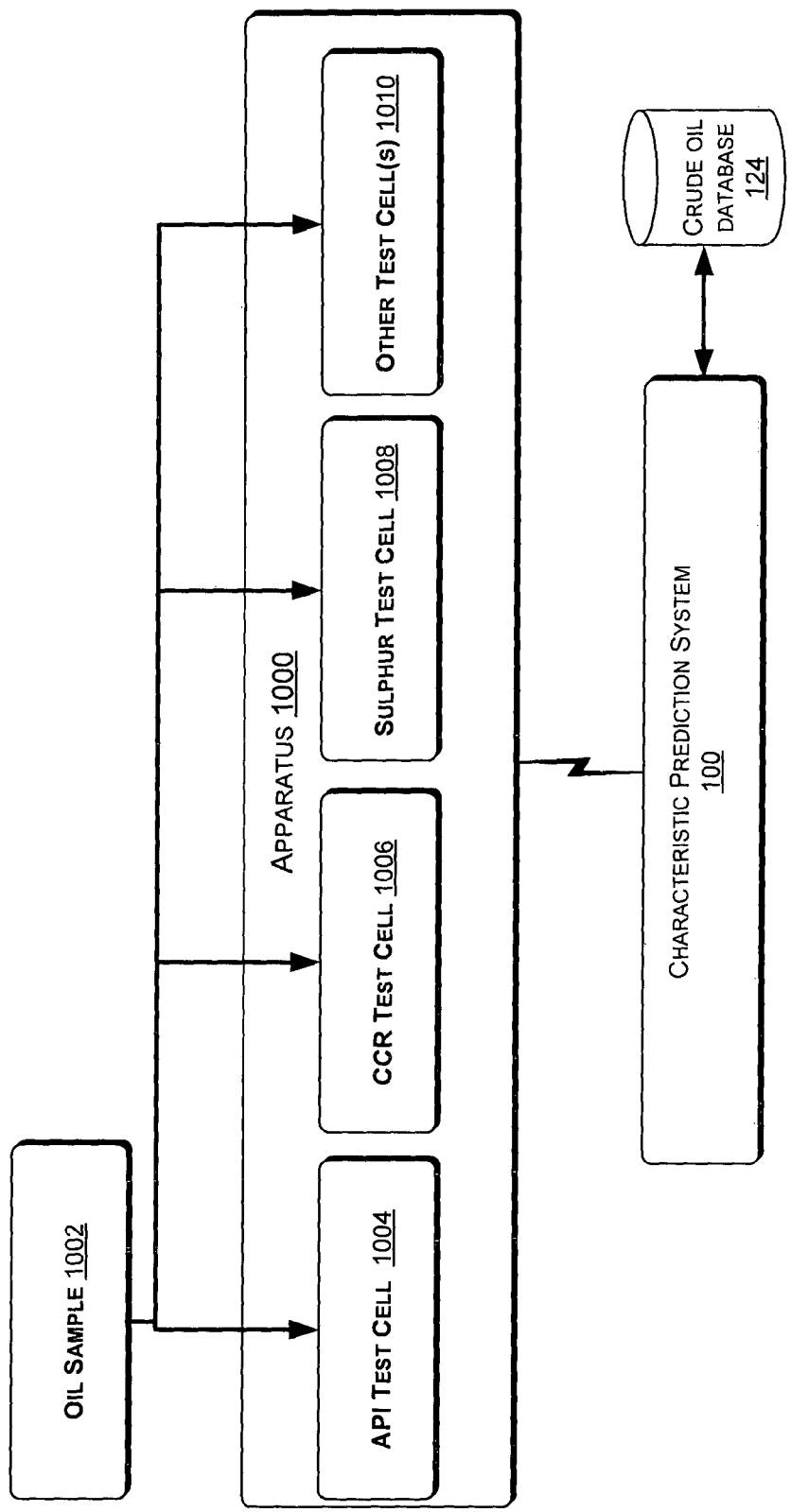
FIG. 10 illustrates an apparatus for measurement of the physical properties of the given oil sample, in accordance with an implementation of the present subject matter.

FIG. 10 illustrates an apparatus 1000 for testing an oil sample 1002 for determination of different physical properties of the oil sample 1002. The apparatus 1000 may comprise of a plurality of test cells, for example, an API test cell 1004, a CCR test cell 1006, and a Sulphur test cell 1008. Further, the apparatus may also comprise other test cell(s) 1010. The apparatus 1000 may be connected to the characteristic prediction system 100, either through a network or directly, in order that the characteristic prediction system 100 may receive determined values of the physical properties of the oil sample 1002 for the prediction of refining characteristics of the oil sample 1002.

In operation, the oil sample 1002 is fed into the apparatus 1000. The oil sample 1002 may be channelized into the apparatus 1000 to ensure that the oil sample 1002 is individually fed into each test cell or the specific test cells selected by a user.

The API test cell 1004 is configured to test the oil sample for determination of the API gravity of the oil sample 1002.

The API test cell may be further configured to store the determined value of the API gravity of the oil sample 1002 in order to provide the value of API gravity to the characteristic prediction system 100. Similarly, the CCR test cell 1006 may be configured to determine and store the value of CCR content of the oil sample 1002. Further, the Sulphur test cell 1008 may be configured to determine and store the value of Sulphur content of the oil sample 1002.

Thus, the apparatus 1000 may be used in a laboratory for performing the tests on the oil sample 1002 for measurement of physical properties in order to predict the refining characteristics, of the oil sample 1002. Furthermore, the other test cell(s) 1010 may be configured to determine and store the value of other physical parameters of the oil sample 1002, such as Carbon content, Hydrogen content, Nitrogen content, Mercaptan value, Kinematic viscosity, Pour point, Ramsbottm Carbon Residue (RCR), Micro Carbon Residue (MCR), Saturates, Aromatics, Resins, and Asphaltenes.

In yet another embodiment of the present subject matter, method(s) and system for predicting hydrogen consumption in hydro processing and intermediate refinery distillate streams as the refining characteristic has also been described. The method of predicting the hydrogen consumption in hydro processing (based on refinery specific configuration and assumptions) and intermediate refinery distillate streams, which may be referred to as the secondary processing characteristics, may include development of a prediction model based on regression. The method may further include determining the physical properties of the oil sample and predicting the refining characteristics based on the developed prediction model. The determination of the physical properties of the oil sample includes determining at least CCR content, RCR and MCR In a further embodiment, the refining characteristic includes potential of production of at least one of bitumen, Fuel Oil (FO) or Low Sulphur Heavy Stock (LSHS) from the oil sample. The bitumen, FO or LSHS may be predicted using the prediction of the vacuum residue as described earlier. The prediction of bitumen. FO or LSHS may then be used to estimate the best possible utilization of the vacuum residue for maximum refinery profitability.

Details of distillation profiles and qualities, obtained as a result of using the above subject matter, as an experiment in a laboratory, for five unknown oil samples are listed below in Tables 4-8. As can be seen, the yield profiles and quality of the different distillate yields can be predicted based on the properties of the crude oil. The present subject matter can also be used for estimation of critical physical properties of crude oils from measurement of at least one of CCR content, RCR and MCR of the oil sample. The critical properties of crude oils include kinematic viscosity, pour point, asphaltenes, mercaptan, volume average boiling point (VABP), molecular weight and UOPK. These properties are valuable for refinery process ability of crude oil samples.

The quality of distillates prediction, e.g., API, Sulphur, Cetane, Flash, Freezing, Smoke, viscosity, pour point, nitrogen, acidity and aniline of the distillates, are also important information for refinery processing for meeting the product and pricing for refining business decisions. The prediction of quality of residue, e.g., asphaltenes, CCR, API, and Sulphur of the residue for best utilization of reside material can be possible. The decision for reside utilization for suitability of bitumen production and fuel oil or low Sulphur heavy stock (LSHS) production is important for value addition at refineries. This can be predicted through measurement of crude oil properties including at least one of CCR content, RCR and MCR.

TABLE 4

Prediction of distillation profile and qualities - Sample 1

| Analyses Details | Unit | Crude | Naphtha | KERO | GO | AR | VGO | VR |
|---|---|---|---|---|---|---|---|---|
| Cuts | — | — | IBP-140 | 140-240 | 240-360 | 360+ | 360-565 | 565+ |
| Yield | % wt | — | 8.19 | 16.87 | 34.74 | 37.25 | 29.35 | 7.9 |
|  | % vol | — | 10.17 | 18.02 | 34.57 | 34.29 | 27.38 | 6.91 |
| API Gravity | — | 28.57 | 68.4 | 39.44 |  | 15.77 | 17.73 | 8.55 |
| Sulphur | % wt | 0.273 | 0.0007 | 0.0682 | 0.26 | 0.479 | 0.4160 | 0.65 |
| Mercaptan | ppm | 18 | 1.98 | 8.6 | — | — | — | — |
| KV @ 40 C. | cSt | 6.05 | — | — | 5.305 | 33.4 @100 | 14.43 @ 100 | — |
| Pour Point | C. | −55 | — | — | −40 | 40 | 29.2 | 69 |
| Acidity | mg/KOH | 0.67 |  | 0.275 | 0.586 | — | 1.06 | — |
| Total Nitrogen | ppm | 1600 | — | — | — | — | — | — |
| Basic Nitrogen | ppm | 550 | — | — | — | — | 842.9 | — |
| Freezing Point | C. | — | — | −77.33 | — | — | — | — |
| Smoke Point | mm | — | — | 24 | — | — | — | — |
| Flash Point | C. | — | 0.2 | 48.4 | 127 | — | — | — |
| Cetane Index | — | — | — | 32.76 | 42.75 | — | — | — |
| Aniline Point | C. | — | — | — | 60.25 | — | — | — |
| Conradson Carbon | % wt | 1.339 | — | — | 0.0472 | 3.10 | 0.421 | — |
| Asphaltenes | % wt | — | — | — | — | 0.750 | 4.4 | — |

TABLE 5

Prediction of distillation profile and qualities - Sample 2

| Analyses Details | Unit | Crude | Naphtha | Kerosene | GO | AR | VGO | VR |
|---|---|---|---|---|---|---|---|---|
| cuts | — | — | IBP-140 | 140-240 | 240-360 | 360+ | 360-565 | 565+ |
| Yield | % wt | — | 0.54 | 9.26 | 47.00 | 42.42 | 36.04 | 6.38 |
|  | % vol | — | 0.64 | 10.05 | 47.48 | 41.07 | 35.06 | 6.01 |
| API Gravity | — | 21.94 | 49.90 | 32.65 | 23.47 | 16.97 | 17.88 | 12.99 |
| Sulphur | % wt | 0.12 | 0.01 | 0.02 | 0.06 | 0.19 | 0.17 | 0.26 |
| Mercaptan | ppm | 15.00 | 4.83 |  | — | — | — | — |

TABLE 5-continued

Prediction of distillation profile and qualities - Sample 2

| Analyses Details | Unit | Crude | Naphtha | Kerosene | GO | AR | VGO | VR |
|---|---|---|---|---|---|---|---|---|
| KV @ 40 C. | cSt | 18.21 | — | — | 6.85 | 18.35 | 11.62 @ 100 C. | — |
| Pour Point | C. | −48.00 | — | — | <−50 | −13.00 | −25.00 | 17.00 |
| Acidity | mg/KOH | 0.43 | — | 0.04 | 0.31 | — | 0.59 | — |
| Total Nitrogen | ppm | — | — | — | — | — | — | — |
| Basic Nitrogen | ppm | 338.00 | — | — | — | — | 560.00 | — |
| Freezing Point | C. | — | — | — | — | — | — | — |
| Smoke Point | mm | — | — | 21.00 | — | — | — | — |
| Flash Point | C. | — | 0.10 | 57.00 | 130.00 | — | — | — |
| Cetane Index | — | — | — | 27.22 | 56.32 | — | — | — |
| Aniline Point | C. | — | — | — | 53.50 | — | — | — |
| Conradson Carbon | % wt | 0.69 | — | — | 0.01 | 1.20 | 0.30 | 10.03 |

TABLE 6

Prediction of distillation profile and qualities - Sample 3

| Analyses Details | Unit | Crude | Naphtha | Kerosene | GO | AR | VGO | VR |
|---|---|---|---|---|---|---|---|---|
| Cuts | — | — | IBP-140 | 140-240 | 240-360 | 360+ | 360-565 | 565+ |
| Yield | % wt | — | 3.085 | 4.9 | 13.61 | 78.43 | 31.79 | 46.64 |
|  | % vol | — | 3.766 | 5.64 | 14.64 | 75.14 | 32 | 43.14 |
| API Gravity | — | 25.59 | 64.3 | 48.72 | 38.08 | 19.2 | 27.07 | 13.83 |
| Sulphur | % wt | 0.117 | 0.0001 | 0.0217 | 0.0576 | 0.143 | 0.0959 | 0.174 |
| Mercaptan | ppm | — | 0.955 | 4 | — | — | — | — |
| KV @ 40 C. | cSt | 26.01 @ 100 C. | — | — | 5.2114 | — | 7.53 @ 100 C. | — |
| Pour Point | C. | 32 | — | — | 0 | 40 | 37 | 42 |
| Acidity | mg/KOH | 3.83 | — | 0.49 | 1.17 | — | 4.32 | — |
| Total Nitrogen | ppm | 2250 | — | — | — | — | — | — |
| Smoke Point | mm | — | — | 33 | — | — | — | — |
| Flash Point | C. | — | −6.9 | 65.3 | — | — | — | — |
| Cetane Index | — | — | — | 53.95 | 66.76 | — | — | — |
| Aniline Point | C. | — | — | — | 56.25 | — | — | — |
| Conradson Carbon | % wt | 10.13 | — | — | 0.0943 | 10.32 | 0.2609 | 16.95 |

TABLE 7

Prediction of distillation profile and qualities - Sample 4

| Analyses Details | Unit | Crude | Naphtha | Kerosene | GO | AR | VGO | VR |
|---|---|---|---|---|---|---|---|---|
| cuts | — | — | IBP-140 | 140-240 | 240-360 | 360+ | 360-565 | 565+ |
| Yield | % wt | — | 7.352 | 16.05 | 21.49 | 48.28 | 26.64 | 21.64 |
|  | % vol | — | 9.693 | 17.76 | 21.75 | 42.82 | 24.88 | 17.94 |
| API Gravity | — | 31.40 | 82.8 | 48.76 | 33.33 | 13.06 | 20.72 | 3.55 |
| Sulphur | % wt | 2.75 | 0.017 | 0.163 | 1.9 | 4.603 | 3.4710 | 6.074 |
| Mercaptan | ppm | — | — | 3.4 | — | — | — | — |
| KV @ 40 C. | cSt | 7.61 | — | — | 4.622 | — | 8.979 @ 100 C. | — |
| Pour Point | C. | −61.0 | — | — | −16.0 | 33 | 26.7 | 40 |
| Acidity | mg/KOH | 0.24 | — | 0.1328 | 0.1715 | — | 0.41 | — |
| Total Nitrogen | ppm | 912 | — | — | — | — | 1085 | — |
| Basic Nitrogen | ppm | 218 | — | — | — | — | 264 | — |
| Freezing Point | C. | — | — | −55.77 | — | — | — | — |
| Smoke Point | mm | — | — | 20 | — | — | — | — |
| Flash Point | C. | — | <0 | 46.60 | — | — | — | — |
| Cetane Index | — | — | — | 35.59 | 49.20 | — | — | — |
| Aniline Point | C. | — | — | — | 61.50 | — | — | — |
| Conradson Carbon | % wt | 5.69 | — | — | 0.0598 | 11.37 | 0.80 | 24.75 |
| Asphaltenes | % wt | — | — | — | — | 7.170 | — | 13.88 |

TABLE 8

Prediction of distillation profile and qualities - Sample 5

| Analyses Details | Unit | Crude | Naphtha | Kerosene | GO | AR | VGO | VR |
|---|---|---|---|---|---|---|---|---|
| cuts | — | — | IBP-140 | 140-240 | 240-360 | 360+ | 360-565 | 565+ |
| Yield | % wt | — | 8.27 | 15.15 | 21.96 | 52.47 | 29.22 | 23.25 |
|  | % vol | — | 10.14 | 16.67 | 27.79 | 48.20 | 27.67 | 20.53 |
| API Gravity | — | 29.66 | 80.8 | 45.35 | 32.39 | 15.22 | 21.27 | 7.23 |

TABLE 8-continued

Prediction of distillation profile and qualities - Sample 5

| Analyses Details | Unit | Crude | Naphtha | Kerosene | GO | AR | VGO | VR |
|---|---|---|---|---|---|---|---|---|
| Sulphur | % wt | 2.191 | 0.021 | 0.2947 | 1.2292 | 2.939 | 2.259 | 3.759 |
| Mercaptan | ppm | 2350 | 46.8 | 233 | — | — | — | — |
| KV @40 C. | cSt | 9.736 | — | — | 4.263 | — | 4.1 @ 100 C. | — |
| Pour Point | C. | −18.00 | — | — | −18.0 | — | 39.00 | 51.00 |
| Acidity | mg/KOH | 1.956 | — | 0.636 | — | 2.73 | 3.82 | — |
| Total Nitrogen | ppm | — | — | — | — | — | — | — |
| Basic Nitrogen | ppm | 270 | — | — | — | 5145 | 3550 | — |
| Freezing Point | C. | — | — | −66.1 | — | — | — | — |
| Smoke Point | mm | — | — | 26.00 | — | — | — | — |
| Flash Point | C. | — | <0 | 50.4 | 126.90 | — | — | — |
| Cetane Index | — | — | — | 42.63 | 51.87 | — | — | — |
| Aniline Point | C. | — | — | 56.25 | 67.15 | — | — | — |
| Conradson Carbon | % wt | 4.32 | — | — | — | — | 0.28 | 18.8 |
| Asphaltenes | % wt | 0.851 | — | — | — | — | — | 9.7 |

Although implementations for prediction of refining characteristics of oil have been described in language specific to structural features and/or methods, it is to be understood that the appended claims are not necessarily limited to the specific features or methods described. Rather, the specific features and methods are disclosed as exemplary implementations for prediction of refining characteristics of oil.

What is claimed is:

1. A method for predicting a refining characteristic of an oil sample of an unknown oil for planning, controlling, and optimizing refinery operation of the unknown oil, the method comprising:
receiving values for a plurality of physical properties of the oil sample, wherein the plurality of physical properties includes carbon residue content measured by at least one of Conradson Carbon Residue (CCR) content, Ramsbottom Carbon Residue (RCR) and Micro Carbon Residue (MCR), and at least one other parameter selected from American Petroleum Institute (API) Gravity and Sulphur content; and
determining the refining characteristic of the oil sample based on a prediction model by using the received values as an input to the prediction model, wherein determining the refining characteristic includes deriving a yield profile with respect to temperature ranges of the oil sample, wherein the yield profile includes yield profile for distillates and the distillates include at least one of Naphtha, Kerosene, Gas oil, and Vacuum Gas oil, wherein an increase in Naphtha and Kerosene production is positively correlated to API gravity and Sulphur content and negatively correlated to Carbon Residue Content, wherein the prediction model is based on coefficients of regression obtained from correlating the refining characteristic with the plurality of physical properties for known crude oils, and outputting the refining characteristic on a display or in a report, wherein the refining characteristic is a characteristic of the unknown oil, and
controlling and optimizing refinery operation of the unknown oil based on the determined refining characteristic and the yield profile, wherein the optimizing refinery operation of unknown oil comprises using the refining characteristic, to accurately make financial and operational business decisions such that greater profitability is achieved.

2. The method as claimed in claim 1, wherein the unknown oil is at least one of a crude oil, synthetic crude oil, an unknown hydrocarbon mixture, and a combination thereof.

3. The method as claimed in claim 1, wherein the refining characteristic is at least one of distillate yield profile, residue yield profile, processability, product qualities, hydrogen consumption in hydro processing, refinery processing cost, and ranking of the unknown oil.

4. The method as claimed in claim 1, wherein the determining the refining characteristic further comprises determining potential of production of at least one of bitumen, Fuel Oil and Low Sulphur Heavy Stock from the oil sample.

5. The method as claimed in claim 1, wherein the refining characteristic comprises at least one of Volume Average Boiling Point (VABP), Universal Oil Characterization Factor (UOP-k), Mean Average Boiling Point (MEABP), molecular weight, kinematic viscosity, asphaltenes, pour point, and mercaptan content of the unknown oil.

6. The method as claimed in claim 1, wherein the plurality of physical properties further includes at least one of Hydrogen content, Nitrogen content, Mercaptan value, Kinematic viscosity, Pour point, Saturates, Aromatics, Resins, and Asphaltenes.

7. The method as claimed in claim 1, wherein the coefficients of regression are calculated based on one of linear regression and non-linear regression.

8. The method as claimed in claim 1, wherein the yield profile includes yield profile for residue, and wherein the residue includes at least one of Atmospheric residue and Vacuum residue.

9. The method as claimed in claim 1, wherein
an increase in Vacuum Gas Oil production is positively correlated to Carbon Residue content and is negatively correlated to API gravity and Sulphur content; and
an increase in Gas Oil production is positively correlated to Sulphur content and negatively correlated to API gravity and Carbon Residue content.

10. The method as claimed in claim 8, wherein an increase in Atmospheric residue production is positively correlated to Carbon Residue content and is negatively correlated to API gravity and Sulphur content.

11. The method as claimed in claim 8, wherein an increase in Vacuum Residue production is positively correlated to Carbon Residue content, negatively correlated to Sulphur content, and is negligibly dependent on API gravity.

12. A characteristics prediction system for predicting the refining characteristic of an oil sample of an unknown oil to plan, control, and optimize refinery operation of the unknown oil, the characteristics prediction system comprising:
- a processor;
- an interface; and
- a memory coupled to the processor, the memory comprising:
  - a receiving module configured to receive values of a plurality of physical properties of the oil sample, wherein the physical properties includes carbon residue content measured by at least one of Conradson Carbon Residue (CCR) content, Ramsbottom Carbon Residue (RCR) and Micro Carbon Residue (MCR), and at least one parameter selected form American Petroleum Institute (API) gravity and Sulphur content;
  - a regression module configured to compute coefficients of regression based on correlation regression of the plurality of physical properties and refining characteristics of known crude oils stored in a Crude oil database, wherein the regression module is further configured to generate a yield prediction model based on negative correlation of increase in Naphtha production, Kerosene production and Gas Oil production with Conradson Carbon Residue (CCR) content, wherein an increase in Naphtha and Kerosene production is positively correlated to API gravity and Sulphur content and negatively correlated to Carbon Residue Content; and
  - a prediction module configured to predict the refining characteristic of the oil sample based on the received values of the plurality of physical properties and the coefficients of regression, and output the refining characteristic on a display or in a report, wherein the refining characteristic is a characteristic of the unknown oil, and
  - wherein the prediction module is further configured to control and to optimize refinery operation of the unknown oil based on the determined refining characteristic and the yield profile, wherein to optimize refinery operation of unknown oil comprises to use the refining characteristic, to accurately make financial and operational business decisions such that greater profitability is achieved.

13. The system as claimed in claim 12, wherein the prediction module is further configured to predict potential of production of at least one of bitumen, Fuel Oil and Low Sulphur Heavy Stock from the oil sample.

14. The system as claimed in claim 12, wherein the refining characteristic comprises at least one of distillate yield profile, residue yield profile, processability, product qualities, hydrogen consumption in hydro processing, refinery processing cost and ranking of the oil sample.

15. The system as claimed in claim 12, wherein the refining characteristic further comprises at least one of Volume Average Boiling Point (VABP), Universal Oil Characterization Factor (UOP-k), molecular weight, kinematic viscosity, asphaltenes, pour point, and mercaptan content of the oil sample.

16. The system as claimed in claim 12, wherein the unknown oil is at least one of a crude oil, synthetic crude oil, unknown hydrocarbon mixture, and a combination thereof.

17. The system as claimed in claim 12, wherein the plurality of physical properties further includes at least one of Hydrogen content, Nitrogen content, Mercaptan value, Kinematic viscosity, Pour point, Saturates, Aromatics, Resins and Asphaltenes.

18. The system as claimed in claim 12, wherein the regression module is further configured to generate a yield prediction model based on a positive correlation of increase in Vacuum Gas Oil production, Atmospheric Residue production, and Vacuum Residue production with Conradson Carbon Residue (CCR) content.

19. An apparatus for testing an oil sample for predicting refining characteristics, the apparatus comprising:
- at least one computer processor;
- an American Petroleum Institute (API) test cell configured to test the oil sample for determining API gravity of the oil sample;
- a Conradson Carbon Residue (CCR) test cell configured to test the oil sample for determining CCR content of the oil sample;
- a Sulphur test cell configured to test the oil sample for determining Sulphur content of the oil sample;
- wherein the apparatus is configured to provide the API gravity of the oil sample, the CCR content of the oil sample, and the Sulphur content of the oil sample to a characteristic prediction system to predict the refining characteristics of the oil sample, wherein the characteristic prediction system predicts the refining characteristic based on correlations between the refining characteristics and the CCR content, the API gravity, and the Sulphur content, wherein the characteristic prediction system further predicts the refining characteristic based on a prediction model by using the API gravity of the oil sample, the CCR content of the oil sample, and the Sulphur content of the oil sample as an input to the prediction model, wherein the prediction model is based on coefficients of regression obtained from correlating the refining characteristics with the plurality of physical properties for known crude oils, and wherein the plurality of physical properties includes at least one of CCR content, Ramsbottom Carbon Residue (RCR), Micro Carbon Residue (MCR), Sulphur content, Carbon content, Hydrogen content, Nitrogen content, API gravity, Mercaptan value, Kinematic viscosity, Pour point, Saturates, Aromatics, Resins, and Asphaltenes, wherein the apparatus is further configured to generate a yield prediction model based on negative correlation of increase in Naphtha production, Kerosene production and Gas Oil production with Conradson Carbon Residue (CCR) content, wherein an increase in Naphtha and Kerosene production is positively correlated to API gravity and Sulphur content and negatively correlated to Carbon Residue Content;
- wherein the apparatus is further configured to output the refining characteristic on a display or in a report, wherein the refining characteristic is a characteristic of the unknown oil, and
- wherein the apparatus is further configured to control and to optimize refinery operation of the unknown oil based on the determined refining characteristic and the yield profile, wherein to optimize refinery operation of unknown oil comprises to use the refining characteristic, to accurately make financial and operational business decisions such that greater profitability is achieved.

20. The apparatus as claimed in claim 19, wherein the apparatus further comprises other test cells configured to test the oil sample to determine at least one of Carbon content, Hydrogen content, Nitrogen content, Mercaptan value, Kinematic viscosity, Pour point, Ramsbottom Carbon Residue (RCR), Micro Carbon Residue (MCR), Saturates, Aromatics, Resins, and Asphaltenes of the oil sample.

* * * * *